(12) United States Patent
Phull et al.

(10) Patent No.: US 9,227,990 B2
(45) Date of Patent: Jan. 5, 2016

(54) ANTIVIRAL PHOSPHONATE ANALOGUES AND PROCESS FOR PREPARATION THEREOF

(71) Applicant: Cipla Limited, Mumbai (IN)

(72) Inventors: Manjinder Singh Phull, Mumabi (IN); Rajendra Narayanrao Kankan, Mumbai (IN); Dharmaraj Ramachandra Rao, Thane (IN)

(73) Assignee: CIPLA LIMITED, Mumbai (IN)

( * ) Notice: Subject to any disclaimer, the term of this patent is extended or adjusted under 35 U.S.C. 154(b) by 0 days.

(21) Appl. No.: 14/439,578

(22) PCT Filed: Oct. 29, 2013

(86) PCT No.: PCT/GB2013/000461
§ 371 (c)(1),
(2) Date: Apr. 29, 2015

(87) PCT Pub. No.: WO2014/068265
PCT Pub. Date: May 8, 2014

(65) Prior Publication Data
US 2015/0291639 A1    Oct. 15, 2015

(30) Foreign Application Priority Data

Oct. 29, 2012 (IN) .......................... 3132/MUM/2012

(51) Int. Cl.
C07D 293/06 (2006.01)
C07H 21/00 (2006.01)
C07F 9/6561 (2006.01)

(52) U.S. Cl.
CPC .................................. C07F 9/65616 (2013.01)

(58) Field of Classification Search
CPC .............................. C07D 293/06; C07H 21/00
See application file for complete search history.

(56) References Cited

U.S. PATENT DOCUMENTS

| | | |
|---|---|---|
| 3,201,387 A | 8/1965 | Heidelberger |
| 3,352,912 A | 11/1967 | Prichard |
| 3,616,208 A | 10/1971 | Howells et al. |
| 3,646,007 A | 2/1972 | Gordon |
| 3,798,209 A | 3/1974 | Witkowski et al. |
| 4,199,574 A | 4/1980 | Schaeffer |
| 4,355,032 A | 10/1982 | Verheyden et al. |
| 4,689,338 A | 8/1987 | Gerster |
| 4,724,232 A | 2/1988 | Rideout et al. |
| 4,808,716 A | 2/1989 | Hol et al. |
| 5,034,394 A | 7/1991 | Daluge |
| 5,075,445 A | 12/1991 | Jarvest et al. |
| 5,130,421 A | 7/1992 | Starrett, Jr. et al. |
| 5,142,051 A | 8/1992 | Holy et al. |
| 5,196,438 A | 3/1993 | Martin et al. |
| 5,206,244 A | 4/1993 | Zahler et al. |
| 5,246,937 A | 9/1993 | Harnden et al. |
| 5,366,972 A | 11/1994 | Hargrave et al. |
| 5,519,021 A | 5/1996 | Young et al. |
| 5,763,483 A | 6/1998 | Bischofberger et al. |
| 6,083,953 A | 7/2000 | Nestor et al. |

FOREIGN PATENT DOCUMENTS

| | | |
|---|---|---|
| IN | 3132MUM2012 | 10/2012 |
| WO | 9109849 A1 | 7/1991 |
| WO | 9116320 A1 | 10/1991 |
| WO | 9117159 A1 | 11/1991 |
| WO | 9214743 A2 | 9/1992 |
| WO | 9405639 A1 | 3/1994 |
| WO | 9414436 A1 | 7/1994 |
| WO | 9428920 A1 | 12/1994 |
| WO | 9509843 A1 | 4/1995 |
| WO | 9530670 A2 | 11/1995 |
| WO | 9721685 A1 | 6/1997 |
| WO | 9740029 A1 | 10/1997 |

(Continued)

OTHER PUBLICATIONS

Arimilli, M. N., et al., "Synthesis, in vitro biological evaluation and oral bioavailability of 9-[2-(phosphonomethoxy) propyl]adenine (PMPA) prodrugs," Antiviral Chemistry & Chemothereapy, 1997, pp. 557-564, vol. 8, No. 6, International Medical Press Ltd.
Hecker, Scott J., et al., "Prodrugs of Phosphates and Phosphonates," Journal of Medicinal Chemistry, 2008, pp. 2328-2345, vol. 51, No. 8, American Chemical Society.
Foreign communication from the priority application—International Search Report and Written Opinion, PCT/GB2013/000461, Dec. 10, 2013, 11 pages.
First page, including abstract, of International Publication No. WO 2005002626 A2, published Jan. 13, 2005, filed as International Application No. PCT/US2004/013283 on Apr. 26, 2004.
Foreign communication from a related counterpart application—International Preliminary Report on Patentability, PCT/GB2013/000461, May 5, 2015, 8 pages.

*Primary Examiner* — Sun Jae Yoo
(74) *Attorney, Agent, or Firm* — Conley Rose, P.C.; Rodney B. Carroll

(57) ABSTRACT

The present invention provides a compound of the Formula (I)

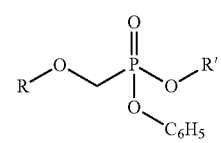

wherein R is 9-isopropyl-9H-purin-6-amine; 2-amino-9-isopropyl-1H-purin-6(9H)-one; 4-amino-1-isopropyl pyrimidin-2(1H)-one; or 1-isopropyl-5-methylpyrimidine-2,4(1H, 3H)-dione, R' is —CH$_2$OC(O)R", and R" is —C(CH$_3$)$_3$ or —CH(CH$_3$)$_2$ including pharmaceutically acceptable salts thereof. The present invention also provides a process for preparing a compound of formula (Ia) and a compound of formula (I) for use in treating a viral infection.

16 Claims, No Drawings

(56) References Cited

FOREIGN PATENT DOCUMENTS

| | | | |
|---|---|---|---|
| WO | 9804569 | A1 | 2/1998 |
| WO | 9933781 | A1 | 7/1999 |
| WO | 9933815 | A1 | 7/1999 |
| WO | 0066558 | A1 | 11/2000 |
| WO | 0190106 | A2 | 11/2001 |
| WO | 0208241 | A2 | 1/2002 |
| WO | 0208244 | A2 | 1/2002 |
| WO | 0218369 | A2 | 3/2002 |
| WO | 03035077 | A1 | 5/2003 |
| WO | 03106461 | A2 | 12/2003 |
| WO | 2014068265 | A1 | 5/2014 |

ANTIVIRAL PHOSPHONATE ANALOGUES AND PROCESS FOR PREPARATION THEREOF

CROSS-REFERENCE TO RELATED APPLICATIONS

This application is a filing under 35 U.S.C. 371 of International Application No. PCT/GB2013/000461 filed Oct. 29, 2013, entitled "Antiviral Phosphonate Analogues and Process for Preparation Thereof," which claims priority to Indian Patent Application No. 3132/MUM/2012 filed Oct. 29, 2012, which applications are incorporated by reference herein in their entirety.

FIELD OF THE INVENTION

The present invention relates to antiviral compounds, including their pharmaceutically acceptable acid addition salts and processes for their preparation.

BACKGROUND OF THE INVENTION

Many challenges are encountered during the development of antiviral agents, including adverse events and the development of drug resistant viruses, which necessitate chemists, biologists, and pharmacologists to develop improved, more potent, and less toxic medicines.

Antiviral compounds are previously reported in U.S. Pat. No. 5,034,394, U.S. Pat. No. 4,199,574, U.S. Pat. No. 4,808, 716, WO 9405639, WO 9740029, WO 0208244, U.S. Pat. No. 5,142,051, WO 03106461, WO 9109849, U.S. Pat. No. 5,519, 021, WO 9214743, WO 9428920, U.S. Pat. No. 5,206,244, U.S. Pat. No. 5,246,937, WO 9933815, U.S. Pat. No. 4,355, 032, U.S. Pat. No. 6,083,953, U.S. Pat. No. 3,646,007, U.S. Pat. No. 4,689,338, WO 9117159, WO 9721685, WO 0190106, WO 9509843, U.S. Pat. No. 5,366,972, U.S. Pat. No. 5,763,483, U.S. Pat. No. 5,075,445, WO 9933781, WO 03035077, U.S. Pat. No. 3,798,209, U.S. Pat. No. 3,352,912, U.S. Pat. No. 5,196,438, WO 9414436, U.S. Pat. No. 5,130, 421, WO 0218369, WO 9804569, U.S. Pat. No. 3,201,387, WO 9530670, U.S. Pat. No. 3,616,208, WO 0066558, U.S. Pat. No. 3,798,209, WO 9116320, U.S. Pat. No. 4,724,232.

Although there are major differences among viruses, specific virological and pharmacological approaches used to develop novel antiviral agents are similar across many viral diseases.

Due to the threat of resistance posed by the known drugs, there is a constant need to update the development pipeline and consider different antiviral drugs.

SUMMARY OF THE INVENTION

According to a first aspect of the present invention, there is provided a compound of the Formula (I)

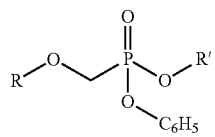

wherein
R is 9-isopropyl-9H-purin-6-amine;
2-amino-9-isopropyl-1H-purin-6(9H)-one;
4-amino-1-isopropyl pyrimidin-2(1H)-one; or
1-isopropyl-5-methylpyrimidine-2,4(1H,3H)-dione,
R' is —CH$_2$OC(O)R", and R" is —C(CH$_3$)$_3$ or —CH(CH$_3$)$_2$.

The compound of formula (I) may be in the form of a free base. The compound of Formula (I) may be in the form of a pharmaceutically active derivative thereof. Preferably, the pharmaceutically acceptable derivative is a salt, solvate, complex, hydrate, isomer, ester, tautomer, anhydrate, diastereomer, polymorph or prodrug. More preferably, the compound of Formula (I) is in the form of a pharmaceutically acceptable acid addition salt thereof.

Examples of the pharmaceutically acceptable acid addition salt of the phosphonate analogs of Formula (I) include, but are not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Preferably, the acid is fumaric acid or tartaric acid. Fumaric acid is more preferably used, but the acid addition salt is not restricted thereto. The salts of the present invention may be crystalline or noncrystalline.

It will be appreciated that around the chiral carbon, the compounds of formula (I) possess the R-stereochemistry, the S-stereochemistry or mixtures thereof. The mixture may comprise any proportion of the R-stereochemistry to the S-stereochemistry, including a 50:50 (i.e. racemic) mixture. Preferably, the compounds of formula (I) are present in enantiomeric excess. More preferably, the compounds of formula (I) are in the form of the R-stereochemistry. Suitably, the compounds of formula (I) possess the R-stereochemistry in at least 90% chiral purity, more preferably greater than 95% chiral purity, most preferably greater than 98% chiral purity yet more preferably greater than 99% chiral purity. Any conventional technique for chiral resolution may be used to form the desired stereochemistry of the compound of formula (I). For example, a mixture of the R- and S-stereomers may be subjected to diastereomeric separation. Diastereomeric separation involves reacting the mixture with a suitable chiral salt to form a mixture of the diastereomer salts, separating the diastereomers, converting the appropriate diastereomer to the desired stereomer. Alternatively, the compound used to prepare the compound of formula (I) may already possess the desired stereochemistry. Preferably, the compound of formula (I) is in the form of the R stereomer at the chiral carbon, and the stereochemistry is introduced via the compound used to prepare the compound of formula (I).

It will also be appreciated that around the phosphorus, the compounds of formula (I) possess the R-stereochemistry, the S-stereochemistry or mixtures thereof. The mixture may comprise any proportion of the R-stereomer to the S-stereomer, including a 50:50 (i.e. racemic) mixture. Preferably, the compounds of formula (I) are present in enantiomeric excess. More preferably, the compounds of formula (I) are in the form of the R-stereomer. Suitably, the compounds of formula (I) are in the form of the R-stereomer having at least 90% chiral purity, more preferably greater than 95% chiral purity, most preferably greater than 98% chiral purity yet more preferably greater than 99% chiral purity. Any conventional technique for chiral resolution may be used to form the desired stereomer of the compound of formula (I) around the phosphorus. For example, a mixture of the R- and S-stereomers may be subjected to diastereomeric separation. Diastereomeric separation involves reacting the mixture with a suitable chiral salt to form a mixture of the diastereomers, separating the diastereomers, converting the appropriate diastereomer to the desired enantiomer. Preferably, the R-enantiomer of the compound of formula (I) is prepared by reacting the mixture with L-(+)-tartaric acid to form diastereomers, separating the R-compound (I). L-tartrate salt from the mixture and converting the salt to the R-enantiomer of the compound of formula (I). Any other suitable chiral acid could be used. HPLC may also be used to separate the enantiomers. Chiral purity refers to the proportion of one enantiomer to another enantiomer; where one enantiomer is in excess, it is a proportion of that enantiomer to the other enantiomer. For example, the chiral purity of an excess of the R enantiomer is expressed as $((R/S) \times 100)\%$. Enantiomeric excess is $(((R-S)/(R+S)) \times 100)\%$.

Thus, the compound of formula (I) may exist as a diastereomer having either the (R,R), (S,S), (R,S) or (S,R) configuration 7. Preferably, the compound of formula (I) is in the form of the (R,R) diastereomer. Preferably, the compound used to prepare the compound (I) possesses the R stereochemistry at the carbon chiral centre. Preferably, the R stereochemistry at the phosphorus is introduced by chiral resolution after the compound (I) is formed.

The present invention provides a compound of Formula (I) as shown above wherein R is 9-isopropyl-9H-purin-6-amine; R' is —CH$_2$OC(O)R", and R" is —C(CH$_3$)$_3$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

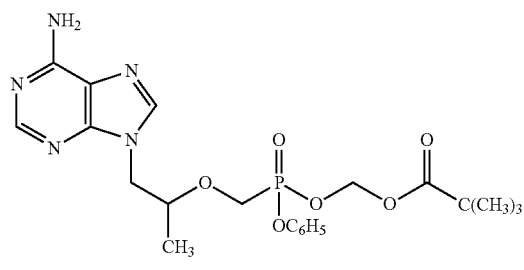

Compound (Ia)

(((1-(6-amino-9H-purin-9-yl)propan-2-yloxy)methyl)(phenoxy)phosphoryloxy)methyl pivalate.

As noted above, the compounds of formula (I) may exist as diastereomers having either the (R,R), (S,S), (R,S) or (S,R) configuration. Preferably, the compound of formula (Ia) is in the form of the (R,R) diastereomer.

The present invention provides a compound of Formula (I) as shown above wherein R is 9-isopropyl-9H-purin-6-amine; R' is —CH$_2$OC(O)R", and R" is —CH(CH$_3$)$_2$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

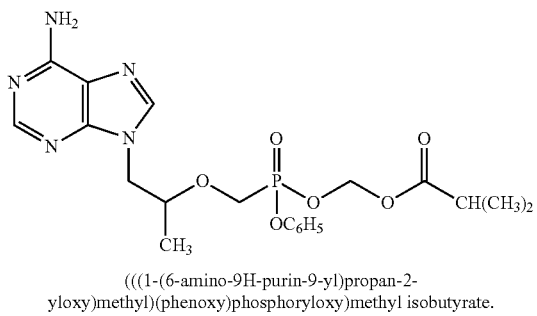

Compound (Ib)

(((1-(6-amino-9H-purin-9-yl)propan-2-yloxy)methyl)(phenoxy)phosphoryloxy)methyl isobutyrate.

As noted above, the compounds of formula (I) may exist as diastereomers having either the (R,R), (S,S), (R,S) or (S,R) configuration. Preferably, the compound of formula (Ib) is in the form of the (R,R) diastereomer.

The present invention provides a compound of Formula (I) as shown above wherein R is 2-amino-9-isopropyl-1H-purin-6(9H)-one; R' is —CH$_2$OC(O)R", and R" is —C(CH$_3$)$_3$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

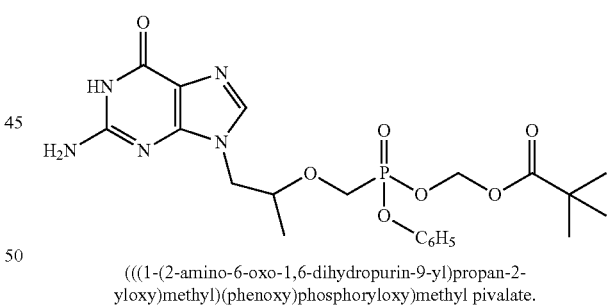

Compound (Ic)

(((1-(2-amino-6-oxo-1,6-dihydropurin-9-yl)propan-2-yloxy)methyl)(phenoxy)phosphoryloxy)methyl pivalate.

As noted above, the compounds of formula (I) may exist as diastereomers having either the (R,R), (S,S), (R,S) or (S,R) configuration. Preferably, the compound of formula (Ic) is in the form of the (R,R) diastereomer.

The present invention provides a compound of Formula (I) as shown above wherein R is 2-amino-9-isopropyl-1H-purin-6(9H)-one; R' is —CH$_2$OC(O)R", and R" is —CH(CH$_3$)$_2$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

Compound (Id)

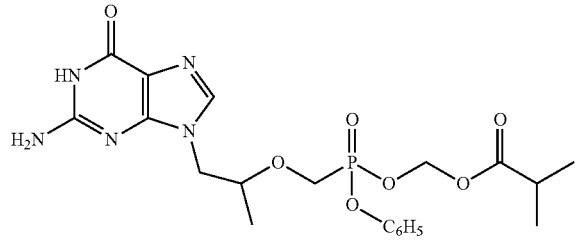

(((1-(2-amino-6-oxo-1,6-dihydropurin-9-yl)-propan-2-yloxy)methyl)(phenoxy)phosphoryloxy)methyl isobutyrate.

As noted above, the compounds of formula (I) may exist as diastereomers having either the (R,R), (S,S), (R,S) or (S,R) configuration. Preferably, the compound of formula (Id) is in the form of the (R,R) diastereomer.

The present invention provides a compound of Formula (I) as shown above wherein R is 4-amino-1-isopropyl pyrimidin-2(1H)-one; R' is —CH$_2$OC(O)R", and R" is —C(CH$_3$)$_3$. Preferably, the compound is in the form of a pharmaceutically acceptable salt thereof. Exemplary salts are listed above. The salt may be the fumaric acid salt or the tartaric acid salt. Most preferably, the free base of the compound is in the form of a fumaric acid addition salt thereof. In this embodiment, the compound has the following structure and name:

Compound (Ie)

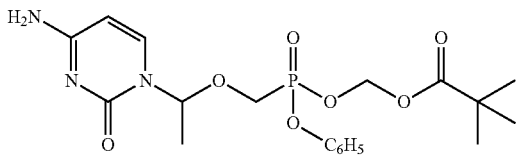

(((1-(4-amino-2-oxopyrimidin-1(2H)-yl)ethoxy)methyl)(phenoxy) phosphoryloxy)methyl pivalate.

As noted above, the compounds of formula (I) may exist as diastereomers having either the (R,R), (S,S), (R,S) or (S,R) configuration. Preferably, the compound of formula (Ie) is in the form of the (R,R) diastereomer.

The present invention provides a compound of Formula (I) as shown above wherein R is 4-amino-1-isopropyl pyrimidin-2(1H)-one; R' is —CH$_2$OC(O)R", and R" is —CH(CH$_3$)$_2$. Preferably, the compound is in the form of a pharmaceutically acceptable salt thereof. Exemplary salts are listed above. The salt may be the fumaric acid salt or the tartaric acid salt. Most preferably, the free base of the compound is in the form of a fumaric acid addition salt thereof. In this embodiment, the compound has the following structure and name:

Compound (If)

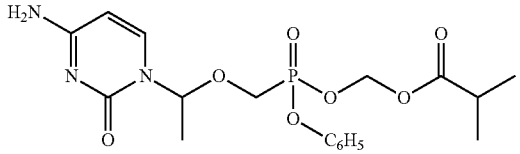

(((1-(4-amino-2-oxopyrimidin-1(2H)-yl)ethoxy)methyl)(phenoxy) phosphoryloxy)methyl isobutyrate.

As noted above, the compounds of formula (I) may exist as diastereomers having either the (R,R), (S,S), (R,S) or (S,R) configuration. Preferably, the compound of formula (If) is in the form of the (R,R) diastereomer.

The present invention provides a compound of Formula (I) as shown above wherein R is 1-isopropyl-5-methylpyrimidine-2,4(1H,3H)-dione; R' is —CH$_2$OC(O)R", and R" is —C(CH$_3$)$_3$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

Compound (Ig)

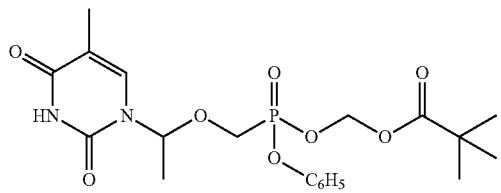

(((1-(5-methyl-2,4-dioxo-3,4-dihydropyrimidin-1(2H)-yl)ethoxy)methyl)(phenoxy)phosphoryloxy)methyl pivalate.

As noted above, the compounds of formula (I) may exist as diastereomers having either the (R,R), (S,S), (R,S) or (S,R) configuration. Preferably, the compound of formula (Ig) is in the form of the (R,R) diastereomer.

The present invention provides a compound of Formula (I) as shown above wherein R is 1-isopropyl-5-methylpyrimidine-2,4(1H,3H)-dione; R' is —CH$_2$OC(O)R", and R" is —CH(CH$_3$)$_2$. Preferably, the compound is in the form of a pharmaceutically acceptable salt thereof. Exemplary salts are listed above. The salt may be the fumaric acid salt or the tartaric acid salt. Most preferably, the compound is in the form of a fumaric acid addition salt thereof. In this embodiment, the free base of the compound has the following structure and name:

Compound (Ih)

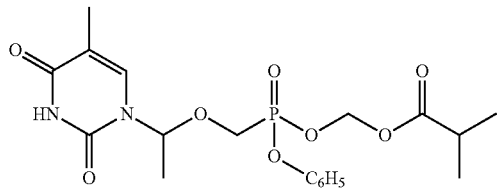

(((1-(5-methyl-2,4-dioxo-3,4-dihydropyrimidin-1(2H)-yl)ethoxy)methyl) (phenoxy)phosphoryloxy)methyl isobutyrate.

As noted above, the compounds of formula (I) may exist as diastereomers having either the (R,R), (S,S), (R,S) or (S,R) configuration. Preferably, the compound of formula (Ih) is in the form of the (R,R) diastereomer.

Preferably, R is 9-isopropyl-9H-purin-6-amine;
R' is CH$_2$OC(O)R"
R" is C(CH$_3$)$_3$
the pharmaceutically acceptable acid addition salt is fumaric acid in the compound of Formula (I) and the compound is in the form of the R,R diastereomer.

According to a second aspect, the present invention provides a method of preparing a compound of Formula (I), which method comprises reacting a compound of Formula (II)

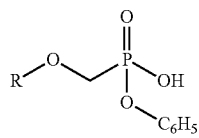

Formula II with a compound of Formula (III)

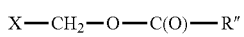

Formula III to obtain a compound of Formula (I),
wherein
R, R" are as previously described; and
X represents a leaving group.

Suitably, the chiral centre on compound (II) already possesses the desired stereochemistry at the chiral carbon; preferably the R-stereochemistry.

Suitably, the compound of Formula (I) is in the form of the free base. Alternatively, the compound of Formula (I) is in the form of a pharmaceutically acceptable acid addition salt thereof, in which case the compounds of Formulae (II) and (III) are reacted together to obtain a compound of Formula (I) in the form of a free base, and the free base is converted to the acid addition salt thereof by reaction with the corresponding acid. For example, the free base of compound (I) may be reacted with fumaric acid to form the corresponding compound (I) in the form of the fumaric acid addition salt thereof. It will be appreciated that other salts may be formed using analogous methods.

The leaving group may be any suitable leaving group. Suitably, the leaving group is a halo group selected from iodo, chloro and bromo; preferably chloro.

In an embodiment, the method is carried out in the presence of a base. Suitably, the base is an auxiliary base whose salts with acids are liberated during the course of the reaction. The auxiliary base can be an inorganic base (such as alkali metal or alkali earth metal carbonates or hydroxides; preferably potassium carbonate or sodium hydroxide) or an organic base, preferably an organic base. The organic base may be: an organic amine such as hexylamine, hexamethylene diamine, benzylamine or a trialkylamine (such as triethylamine); pyridine; or dimethyl pyridine. The organic base is preferably a tertiary amine, in particular a trialkylamine. Preferably, the base is N,N-diisopropylethylamine.

The reaction of compound of Formula (II) and compound of Formula (III) may be carried out in the presence of a solvent selected from a polar aprotic solvent or mixtures thereof. The solvent may be acetonitrile, methylene dichloride, toluene, dimethylformamide, N-methylpyrrolidone or mixtures thereof. Preferably, the solvent is N-methylpyrrolidone.

Preferably, the reaction of compound of Formula (II) and compound of Formula (III) is carried out in the presence of a base as described above and a solvent as described above. Preferably, the base is solvent is N,N-diisopropylethylamine and the solvent is N-methylpyrrolidone.

Around the phosphorus, the compound of formula (I) may be prepared in the form of the R-enantiomer, the S-enantiomer or a mixture thereof. The mixture may comprise any proportion of the R-enantiomer to the S-enantiomer, including a 50:50 (i.e. racemic) mixture. Preferably, the compounds of formula (I) are prepared in enantiomeric excess. More preferably, the compounds of formula (I) are prepared in the form of the R-enantiomer. Suitably, the compounds of formula (I) are in the form of the R-enantiomer having at least 90% chiral purity, more preferably greater than 95% chiral purity, most preferably greater than 98% chiral purity yet more preferably greater than 99%.

In an embodiment, the method comprises chiral resolution of the compound of formula (I) to form the desired diastereomer of the compound of formula (I). The chiral resolution may involve diastereomeric separation with a suitable chiral salt to form a mixture of the diastereomers, separating the diastereomers, and conversion of the appropriate diastereomer to the desired enantiomer. Preferably, the R-enantiomer of the compound of formula (I) is prepared by reacting a mixture of the enantiomers with L-(+)-tartaric acid to form diastereomers, separating the R-compound (I). L-tartrate salt from the mixture and converting the salt to the R-enantiomer of the compound of formula (I).

The method may involve the following steps in this sequence:
reaction of compounds II and III (compound II in the R stereochemistry around the C atom) to form the free base of compound I
converting the free base of compound I to a salt thereof (for example the fumaric acid salt)
reacting the salt of the compound of formula I with a chiral acid (for example L-tartaric acid) to form a diastereomeric mixture
separating the diastereomers
reacting the R-enantiomer/L-tartrate salt with a base to form the R,R-diastereomer of compound I in free base or salt form.

The method may involve the following steps in this sequence:
reaction of compounds II and III (compound II in the R stereochemistry around the C atom) to form the free base of compound I
reacting the free base of the compound of formula I with a chiral acid (for example L-tartaric acid) to form a diastereomeric mixture
separating the diastereomers
reacting the R-enantiomer/L-tartrate salt with a base to form the R,R-diastereomer of compound I in free base or salt form.

It will be appreciated that the resolved compound of formula I may be prepared in the form of the free base and optionally converted to a pharmaceutically acceptable salt thereof by any method described herein. The resolved compound of formula I may be prepared in the form of a salt of compound I and optionally converted to a different, pharmaceutically acceptable salt thereof by any method described herein.

According to another aspect of the present invention, there is provided compounds of Formula (I) as described above prepared according to a method as described above.

According to another aspect of the present invention, there is provided fumaric acid salt of (((1-(6-amino-9H-purin-9-yl) propan-2-yloxy)methyl)(phenoxy)phosphoryloxy)methyl pivalate prepared according to the process of the present invention.

According to another aspect of the present invention, there is provided a pharmaceutical composition comprising a compound of Formula (I) as described above together with one or more pharmaceutically acceptable carriers. Preferably, the compound is (((1-(6-amino-9H-purin-9-yl)propan-2-yloxy)methyl)(phenoxy)phosphoryloxy)methyl pivalate. More preferably, the compound is the fumaric acid salt of (((1-(6-amino-9H-purin-9-yl)propan-2-yloxy)methyl)(phenoxy)phosphoryloxy)methyl pivalate. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided a pharmaceutical composition comprising fumaric acid salt of (((1-(6-amino-9H-purin-9-yl)propan-2-yloxy)methyl)(phenoxy)phosphoryloxy)methyl pivalate together with one or more pharmaceutically acceptable carriers. Suitably, the fumaric acid salt of (((1-(6-amino-9H-purin-9-yl)propan-2-yloxy)methyl)(phenoxy)phosphoryloxy)methyl pivalate has been prepared by any method described herein. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided a compound of Formula (I) as described above or a pharmaceutical composition comprising a compound of Formula (I) as described above together with one or more pharmaceutically acceptable carriers for use in treating viral infections. Preferably, the compound is (((1-(6-amino-9H-purin-9-yl)propan-2-yloxy)methyl)(phenoxy)phosphoryloxy)methyl pivalate. More preferably, the compound is the fumaric acid salt of (((1-(6-amino-9H-purin-9-yl)propan-2-yloxy)methyl)(phenoxy)phosphoryloxy)methyl pivalate. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided the fumaric acid salt of (((1-(6-amino-9H-purin-9-yl)propan-2-yloxy)methyl)(phenoxy)phosphoryloxy)methyl pivalate for use in treating viral infections. Suitably, the fumaric acid salt of (((1-(6-amino-9H-purin-9-yl)propan-2-yloxy)methyl)(phenoxy)phosphoryloxy)methyl pivalate has been prepared by any method described herein. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided the use of a compound of Formula (I) as described above or a pharmaceutical composition comprising a compound of Formula (I) as described above together with one or more pharmaceutically acceptable carriers in the manufacture of a medicament for the treatment of viral infections. Preferably, the compound is (((1-(6-amino-9H-purin-9-yl)propan-2-yloxy)methyl)(phenoxy)phosphoryloxy)methyl pivalate. More preferably, the compound is the fumaric acid salt of (((1-(6-amino-9H-purin-9-yl)propan-2-yloxy)methyl)(phenoxy)phosphoryloxy)methyl pivalate. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided the use of fumaric acid salt of (((1-(6-amino-9H-purin-9-yl)propan-2-yloxy)methyl)(phenoxy)phosphoryloxy)methyl pivalate in the manufacture of a medicament for the treatment of viral infections. Suitably, the fumaric acid salt of (((1-(6-amino-9H-purin-9-yl)propan-2-yloxy)methyl)(phenoxy)phosphoryloxy)methyl pivalate has been prepared by any method described herein. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

According to another aspect of the present invention, there is provided a method of treating a viral infection, the method comprising administering to a subject in need thereof a therapeutically effective amount of fumaric acid salt of (((1-(6-amino-9H-purin-9-yl)propan-2-yloxy)methyl)(phenoxy)phosphoryloxy)methyl pivalate. Suitably, the fumaric acid salt of (((1-(6-amino-9H-purin-9-yl)propan-2-yloxy)methyl)(phenoxy)phosphoryloxy)methyl pivalate has been prepared by any method described herein. Yet more preferably, the compound is the fumaric acid salt of (((1-(6-amino-9H-purin-9-yl)propan-2-yloxy)methyl)(phenoxy)phosphoryloxy)methyl pivalate in the R,R diastereomeric form.

DETAILED DESCRIPTION OF THE INVENTION

The invention relates to antiviral compounds of Formula (I):

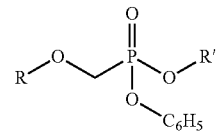

wherein

R is 9-isopropyl-9H-purin-6-amine; 2-amino-9-isopropyl-1H-purin-6(9H)-one; 4-amino-1-isopropyl pyrimidin-2(1H)-one or 1-isopropyl-5-methylpyrimidine-2,4(1H,3H)-dione R' is $CH_2OC(O)R''$ R'' is $C(CH_3)_3$ or $CH(CH_3)_2$ Included within the scope of the invention are the pharmaceutically acceptable acid addition salts of the compounds of Formula (I).

Examples of the pharmaceutically acceptable acid addition salt of the phosphonate analogs of Formula (I) include, but are not limited to, inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, fumaric acid is more preferably used, but the acid addition salt is not restricted thereto. The salts of the present invention may be crystalline or noncrystalline.

In an embodiment, in the compound of general Formula (I):

R is 9-isopropyl-9H-purin-6-amine;

R' is $CH_2OC(O)R''$

R'' is $C(CH_3)_3$.

A preferred example of a compound of Formula (I) is a compound of Formula (Ia):

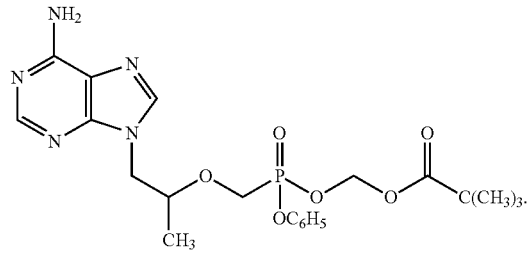

Formula Ia

In another embodiment, the pharmaceutically acceptable acid addition salt of the phosphonate analog of Formula (Ia) is fumaric acid.

In yet another embodiment, the pharmaceutically acceptable acid addition salt of the phosphonate analog of Formula (Ia) is tartaric acid.

Further, the invention relates to the method for preparing compounds of general formula (I), which comprises reacting compound of Formula (II)

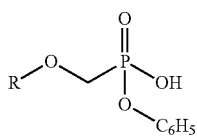

Formula II with a compound of Formula (III)

$$X-CH_2-O-C(O)-R''$$

Formula III and recovering a compound of Formula (I),
wherein
R, R" are as previously described;
X represents a leaving group.

The process of the invention described here is suitably carried out in the presence of an auxiliary base whose salts with acids are liberated during the course of the reaction. The auxiliary base scavenges the acid formed in the reaction giving the desired product in high yield.

The auxiliary base can be inorganic or organic base, preferably organic base. The auxiliary bases are preferably tertiary amines, in particular trialkylamines.

Further, the auxiliary base can be employed individually or in mixtures with one another. The auxiliary base is chosen in such a way that it has no decomposing effect on the product.

The reaction of compound of Formula (II) and compound of Formula (III) is suitably carried out in the presence of a solvent selected from polar aprotic solvent or mixtures thereof.

In an embodiment, the present invention relates to process for preparing compound of Formula (Ia) comprises reacting compound of Formula IIa with compound of Formula IIIa.

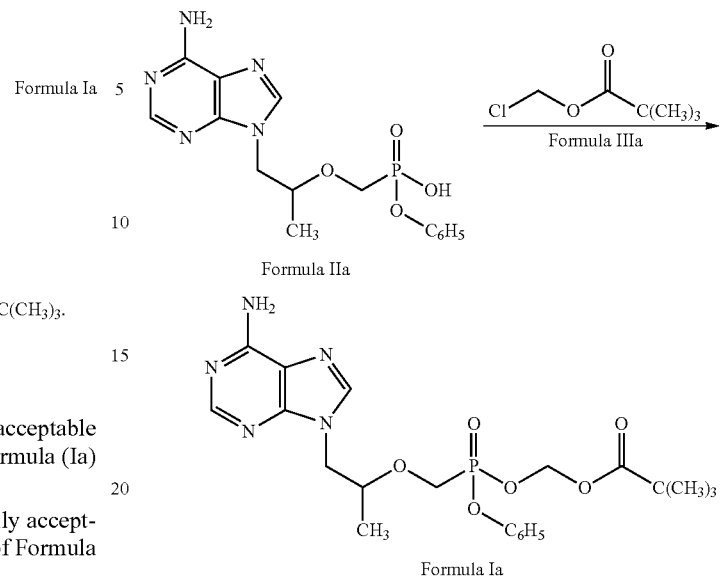

In a further embodiment, the present invention relates to a process for preparing the fumaric salt of compound of Formula (Ia) which comprises reacting the free base of a compound of Formula (Ia) with fumaric acid.

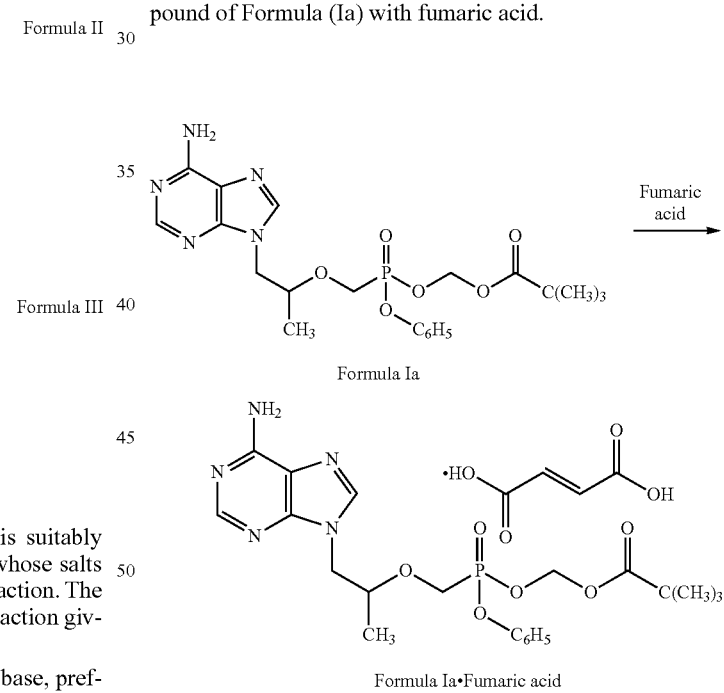

The method may further comprise chiral resolution of the compound of formula Ia to produce the compound in enantiomeric excess. Preferably, the method further comprises chiral resolution of the compound of formula (Ia) to produce the compound in the form of the R,R diastereomer.

In yet another embodiment, the present invention relates to a process for preparing the tartaric salt of compound of Formula (Ia) which comprises reacting the free base of a compound of Formula (Ia) with tartaric acid.

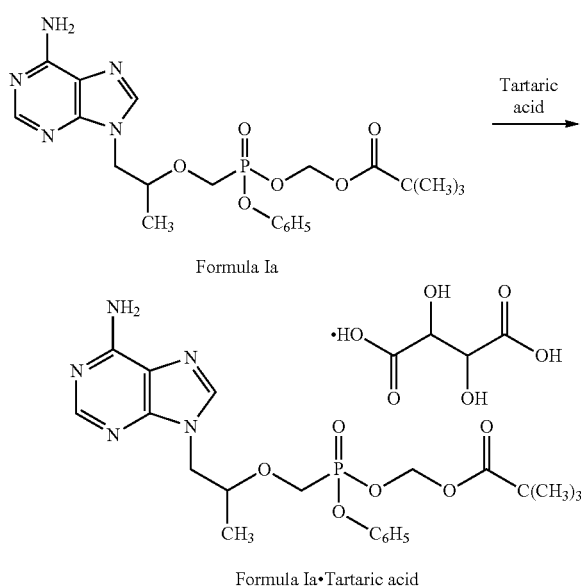

Formula Ia

Formula Ia·Tartaric acid

The present invention also relates to the fumaric acid salt of (((1-(6-amino-9H-purin-9-yl)propan-2-yloxy)methyl)(phenoxy)phosphoryloxy)methyl pivalate preferably in the form of pharmaceutical preparations for use in the treatment of viral infections.

The compounds of the present invention are administered by any route appropriate to the condition to be treated, suitable routes including oral, rectal, nasal, pulmonary, topical, vaginal and parenteral.

The formulations of the present invention comprise compound of general Formula (I) or pharmaceutically acceptable acid addition salt thereof, together with one or more pharmaceutically acceptable carriers and optionally other therapeutic ingredients. The carrier(s) must be "acceptable" in the sense of being compatible with the other ingredients of the formulation and not harmful to the patient.

The following examples, which include preferred embodiments, will serve to illustrate the practice of this invention, it being understood that the particulars shown are by way of example and for purpose of illustrative discussion of preferred embodiments of the invention.

EXAMPLES

Process for preparing phenyl hydrogen ((R)-1-(6-amino-9H-purin-9-yl)propan-2-yloxy)methylphosphonate To a reactor N-methyl pyrrolidone (7500 ml), 9-[2-(phosphonyl methoxy)propyl]adenine (2.5 kg), phenol (1.7 kg) and triethylamine (1500 ml) was added at 20-25° C. and the contents were stirred for 15 minutes. The reaction mass was heated to 80-85° C. and stirred to obtain clear solution. To this a solution of N,N'-Dicyclohexylcarbodiimide in N-methylpyrrolidone was added dropwise. After completion of addition, the reaction mass was heated at 95-100° C. for 2 hours. The reaction mass was cooled and water (5000 ml) was added. The reaction mass was filtered and the residue was washed with water (2500 ml). The filtrate was concentrated under vacuum below 60° C. and diluted with water (5000 ml). The pH was adjusted to 11-11.5. The reaction mass was washed with ethyl acetate and layers were separated. The pH of aqueous layer was adjusted to 2.8-3.2. The reaction mass was stirred, filtered and washed with water followed by methanol. The solid obtained was dried at 45-50° C. to obtain the title compound (Yield—1.6 kg).

Process for preparing fumaric acid salt of (((1-(6-amino-9H-purin-9-yl)propan-2-yloxy)methyl)(phenoxy)phosphoryloxy)methyl pivalate N,N-diisopropylethylamine (35 ml) was added to a reactor containing phenyl hydrogen ((R)-1-(6-amino-9H-purin-9-yl)propan-2-yloxy)methylphosphonate (25 g) and N-methyl pyrrolidone (100 ml). The reaction mass was stirred and heated to 58-62° C. To this 50 ml chloromethyl pivalate was added dropwise and reaction mass was stirred. 500 ml water was added and contents were allowed to settle. The reaction mass was extracted with dichloromethane (250 ml). The organic layer was concentrated under vacuum at 15-20° C. The thick oil obtained was stirred and dissolved in isopropyl alcohol. Fumaric acid (10 g) was added and the contents were heated until total dissolution of fumaric acid. The reaction mass was concentrated and 75 ml acetonitrile was added. The clear solution was cooled, filtered and washed with cold acetonitrile. The solid obtained was dried under vacuum at 30-35° C. to obtain the title compound (Yield—13 g).

Process for preparing tartaric acid salt of (((1-(6-amino-9H-purin-9-yl)propan-2-yloxy)methyl)(phenoxy)phosphoryloxy)methyl pivalate N,N-diisopropylethylamine (25 ml) was added to a reactor containing phenyl hydrogen ((R)-1-(6-amino-9H-purin-9-yl)propan-2-yloxy)methylphosphonate (18 g) and N-methyl pyrrolidone (72 ml). The reaction mass was stirred and heated to 58-62° C. To this 35 ml chloromethyl pivalate was added dropwise and reaction mass was stirred. 360 ml water was added and contents were allowed to settle. The reaction mass was extracted with dichloromethane (180 ml). The organic layer was concentrated under vacuum at 15-20° C. The thick oil obtained was stirred and dissolved in isopropyl alcohol. L-Tartaric acid (5 g) was added and the contents heated at 60° C. to obtain a clear solution. The solution was cooled, filtered and washed with acetonitrile. The solid obtained was dried under vacuum at 30-35° C. to obtain the title compound (Yield—6 g).

Process for preparing (((1-(6-amino-9H-purin-9-yl)propan-2-yloxy)methyl)(phenoxy)phosphoryloxy)methyl pivalate To a reactor N-methyl pyrrolidone (150 ml), 9-[2-(phosphonyl methoxy)propyl]adenine (50 g), phenol (34 g) and triethylamine (30 ml) was added at 20-25° C. and the contents were stirred for 15 minutes. The reaction mass was heated to 80-85° C. and stirred to obtain clear solution. To this a solution of N,N'-Dicyclohexylcarbodiimide in N-methylpyrrolidone was added dropwise. After completion of addition, the reaction mass was heated at 95-100° C. for 2 hours. The reaction mass was cooled and water (100 ml) was added. The reaction mass was filtered and the residue was washed with water (50 ml). The filtrate was concentrated under vacuum below 60° C. and diluted with water (100 ml). The pH was adjusted to 11-11.5. The reaction mass was washed with ethyl acetate and layers were separated. The pH of aqueous layer was adjusted to 2.8-3.2. The reaction mass was stirred, filtered and washed with water followed by methanol. The solid obtained was dried at 45-50° C.

The dried compound (32 g), chloromethyl pivalate (64 ml) and N,N-diisopropylethylamine (480 ml) was heated to 55-60° C. for 4 hours. The reaction mass was cooled and quenched with 80 ml water. The reaction mass was extracted with dichloromethane. The organic layer was collected and distilled under vacuum. To the residue, water (64 ml) was added and contents heated at 50-55° C. for 2 hr. The material was cooled, filtered, washed with water and dried at 40-45° C. to obtain (((1-(6-amino-9H-purin-9-yl)propan-2-yloxy)methyl)(phenoxy)phosphoryloxy)methyl pivalate (Yield—23 g).

Diastereomer Separation of (((1-(6-amino-9H-purin-9-yl)propan-2-yloxy)methyl)(phenoxy)phosphoryloxy)methyl pivalate In a round bottom flask, fumaric acid salt of ((R)-((1-(6-amino-9H-purin-9-yl)propan-2-yloxy)methyl)(phenoxy) phosphoryloxy)methyl pivalate (50 g), water (500 ml) and liquid ammonia (50 ml) at 23-25° C. The reaction mass was stirred for 30 minutes and extracted with dichloromethane (500 ml). The organic layer was collected and distilled under vacuum. To the residue, 135 ml water and 27 ml acetonitrile was added. The contents were stirred at 23-25° C. for 15 minutes. L-tartaric acid (4.25 g) was added and stirred at 55-60° C. The material was filtered, washed with acetonitrile and dried at 40-45° C. to obtain ((R)—(((R)-1-(6-amino-9H-purin-9-yl)propan-2-yloxy)methyl)(phenoxy)phosphoryloxy)methyl pivalate L-tartarate. (Yield—10 g, 80% diastereomeric purity). The solid was purified with water and acetonitrile to obtain ((R)—(((R)-1-(6-amino-9H-purin-9-yl)propan-2-yloxy)methyl)(phenoxy)phosphoryloxy)methyl pivalate L-tartarate (Yield—7 g, 95% diastereomeric purity).

The solid was treated with water and liquid ammonia. The reaction mass was stirred and extracted with dichloromethane. The organic layer was distilled and residue was stirred in water (30 ml) to obtain ((R)—(((R)-1-(6-amino-9H-purin-9-yl)propan-2-yloxy)methyl)(phenoxy)phosphoryloxy)methyl pivalate (Yield—4.5 g, 95% diastereomeric purity).

Diastereomer Separation of (((1-(6-amino-9H-purin-9-yl)propan-2-yloxy)methyl)(phenoxy)phosphoryloxy)methyl pivalate ((R)-((1-(6-amino-9H-purin-9-yl)propan-2-yloxy)methyl)(phenoxy)phosphoryloxy)methyl pivalate was chromatographed by reverse phase HPLC to separate the diastereomers using—

Mobile phase: Solution A:Solution B (Variable Proportion)
Solution A: 0.1% Triethylamine pH-3.0 with Orthophosphoric acid.
Solution B: Acetonitrile
Column: ACE3 C18 PFP (100 mm×4.6 mm×3 μm)
Column Temperature: 25° C.
Flow rate: 1.0 ml/minute.
Detector: 260 nm
Injection Volume: 5 μl
Diluent: Solution A:Solution B (90:10) Premix
Sample Concentration: 1000 ppm
Gradient program:

| Time | % B |
|---|---|
| 0.0 | 20 |
| 5.0 | 20 |
| 20.0 | 30 |
| 25.0 | 65 |
| 30.0 | 65 |
| 32.0 | 20 |
| 35.0 | 20 |

Retention Times: About 17.2 min
About 17.8 min ((R)—(((R)-1-(6-amino-9H-purin-9-yl)propan-2-yloxy)methyl)(phenoxy)phosphoryloxy)methyl pivalate)

Antiviral Activity

The compound of present invention was dosed to animals at human equivalent dose of 300 mg. The Cmax values and the AUC values are shown in the table below.

| Compound | Cmax (% CV) | $AUC_{0-t}$ | $AUC_{0-inf}$ |
|---|---|---|---|
| Fumaric acid salt of (((1-(6-amino-9H-purin-9-yl)propan-2-yloxy)methyl) (phenoxy) phosphoryloxy)methyl pivalate | 548 (25%) | 1167.4 | 1751.1 |
| 2-(Adenin-9-yl)-1(R)-methylethoxy methylphosphonic acid bis(isopropoxycarbonyloxymethyl)ester fumarate | 739.13 (30%) | 1858.45 | 2113.74 |

Cmax = the peak plasma concentration of drug after administration
CV = Coefficient of Variation
$AU_{0-t}$ = area under the plasma concentration-time curve from time zero to the last measurable concentration
$AUC_{0-inf}$ = area under the plasma concentration-time curve from time zero to infinity time It is concluded that the compound of the present invention has a max value comparable with the well known antiviral drug 2-(Adenin-9-yl)-1(R)-methyl ethoxymethylphosphonic acid bis(isopropoxycarbonyloxymethyl)ester fumarate. The compound of the present invention does possess antiviral activity.

It will be appreciated that the invention may be modified within the scope of the appended claims.

The invention claimed is:
1. A compound of Formula (Ia)

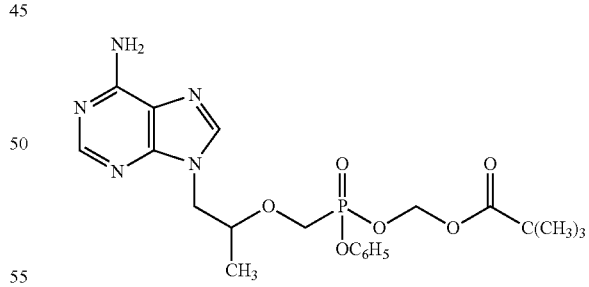

or a pharmaceutically acceptable acid addition salt thereof.

2. The compound according to claim 1, wherein the pharmaceutically acceptable acid addition salt is selected from hydrochloric acid, sulfuric acid, nitric acid, hydrobromic acid, hydroiodic acid, phosphoric acid, acetic acid, lactic acid, citric acid, oxalic acid, glutaric acid, malic acid, tartaric acid, fumaric acid, mandelic acid, maleic acid, benzoic acid, phthalic acid, methanesulfonic acid, ethanesulfonic acid, benzenesulfonic acid, p-toluenesulfonic acid and camphorsulfonic acid.

3. A compound of formula

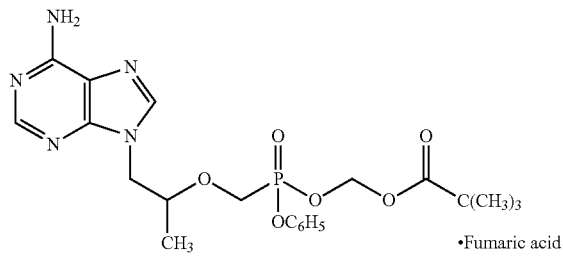
•Fumaric acid

4. The compound according to claim 1, wherein the compound is in the form of the R,R-diastereomer.

5. The compound according to claim 4, wherein the compound in the form of the R,R-diastereomer has a chiral purity of at least 95%.

6. A method of preparing a compound of Formula (Ia) as defined in claim 1, the method comprising reacting a compound of Formula (IIa) with a compound of Formula (IIIa) to obtain a compound of Formula (Ia)

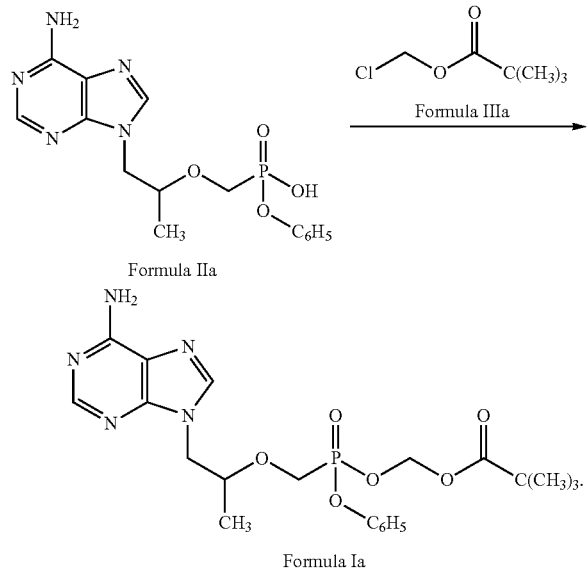

7. The method according to claim 6, wherein the compound of Formula (Ia) is:

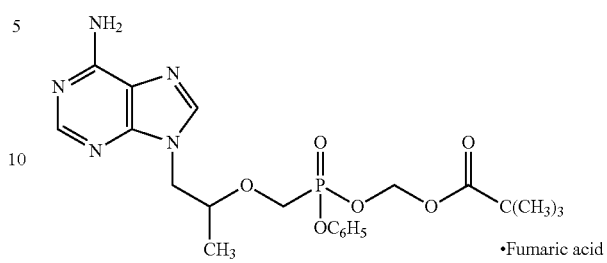
•Fumaric acid and the method comprises reacting the compound of Formula (IIa) with the compound of Formula (IIIa) to obtain the free base of the compound of Formula (Ia), and reacting the free base of the compound of formula (Ia) with fumaric acid to obtain the fumaric acid salt thereof.

8. The method according to claim 6, wherein the compound of formula (Ia) is in the form of the R-enantiomer, and the method comprises a chiral resolution step.

9. A pharmaceutical composition comprising a compound as defined in claim 1 together with a pharmaceutically acceptable carrier.

10. A method of treating a viral infection comprising administering to a patient in need thereof a therapeutically effective amount of a compound as defined in claim 1.

11. L-tartrate salt of (((1-(6-amino-9H-purin-9-yl)propan-2-yloxy)methyl)(phenoxy)phosphoryloxy)methyl pivalate.

12. A method of treating a viral infection comprising administering to a patient in need thereof a therapeutically effective amount of a pharmaceutical composition as defined in claim 9.

13. The compound according to claim 3, wherein the compound is in the form of the R,R-diastereomer.

14. The compound according to claim 13, wherein the compound in the form of the R,R-diastereomer has a chiral purity of at least 95%.

15. The method according to claim 7, wherein the compound of formula (Ia) is in the form of the R-enantiomer, and the method comprises a chiral resolution step.

16. A pharmaceutical composition comprising a compound as defined in claim 3 together with a pharmaceutically acceptable carrier.

* * * * *